US005529904A

United States Patent [19]
Ginsburg et al.

[11] Patent Number: 5,529,904
[45] Date of Patent: *Jun. 25, 1996

[54] DIAGNOSTIC KIT AND DIAGNOSTIC METHOD FOR MYCOPLASMA UTILIZING CARBOHYDRATE RECEPTORS

[75] Inventors: Victor Ginsburg, Bethesda, Md.; Howard C. Krivan, Santa Barbara, Calif.; David D. Roberts, Rockville, Md.

[73] Assignee: The United States of America as represented by the Secretary of the Department of Health and Human Services, Washington, D.C.

[ * ] Notice: The term of this patent shall not extend beyond the expiration date of Pat. No. 5,089,479.

[21] Appl. No.: 79,387

[22] Filed: Jun. 21, 1993

Related U.S. Application Data

[63] Continuation of Ser. No. 417,691, Oct. 5, 1989, Pat. No. 5,225,330, which is a continuation-in-part of Ser. No. 277,634, Nov. 28, 1988, Pat. No. 5,089,479, and a continuation-in-part of Ser. No. 226,445, Aug. 1, 1988, Pat. No. 5,217,715.

[51] Int. Cl.[6] .................. G01N 33/554; G01N 33/569
[52] U.S. Cl. .................. 435/7.32; 435/7.9; 435/870; 435/975; 436/518; 514/2; 514/8; 514/23
[58] Field of Search .................. 435/7.32, 7.9, 435/970, 975, 29, 177, 178, 805, 810, 870; 436/518, 531, 534; 530/395, 399, 412, 413; 514/8, 23, 25, 59

[56] References Cited

U.S. PATENT DOCUMENTS

| | | | |
|---|---|---|---|
| 3,234,096 | 2/1966 | Pollack | 436/818 |
| 4,016,250 | 4/1977 | Saxena | 436/504 |
| 4,123,343 | 10/1978 | Krupey et al. | 204/182.8 |
| 4,280,816 | 7/1981 | Elahi . | |
| 4,351,824 | 9/1982 | Lehrer | 436/508 |
| 4,355,102 | 10/1982 | Quash | 435/5 |
| 4,374,925 | 2/1983 | Litman et al. | 435/7.91 |
| 4,391,904 | 7/1983 | Litman et al. . | |
| 4,565,789 | 1/1986 | Liotta et al. | 436/504 |
| 4,722,887 | 2/1988 | Fabricant et al. | 435/2 |
| 4,727,019 | 2/1988 | Valkirs et al. | 435/5 |
| 4,774,174 | 9/1988 | Giegel et al. | 435/5 |
| 4,855,227 | 8/1989 | McGarrity et al. | 435/7.32 |
| 4,863,852 | 9/1989 | Wilkins et al. . | |
| 4,921,788 | 5/1990 | Deutsch . | |
| 4,959,303 | 9/1990 | Milburn et al. . | |
| 4,990,597 | 2/1991 | Löbermann | 530/392 |
| 5,015,583 | 5/1991 | Pâques | 435/212 |
| 5,158,870 | 10/1992 | Baseman et al. | 435/7.32 |

FOREIGN PATENT DOCUMENTS

0323692  8/1988  European Pat. Off. .

OTHER PUBLICATIONS

Krivan et al, "Patients Bind Specifically to . . . ", Sep. 9, 1987, pp. 493–496.
Krivan et al, "Many Pulmonary Pathogens . . . ", abs. No. B–163.
Kyogashima et al, Archives of Biochemistry and Biophysics, vol. 270, No. 1, Apr. 1989.
Jimenez et al, 1989 ASM Annual Meeting, New Orelans, LA, May 14–18, 1989, Abstract.
Roberts et al, Abstract, Glycoconjugate Journal, vol. 5, p. 350 (1988).
De Man et al, Journal of Clinical Microbiology, vol. 25, No. 2, pp. 401–406, Feb. 1987.
Oellerich, J. Clin. Chem. Clin. Biochem., vol. 22, pp. 895–904 (1984).
Kyogashima et al, Biol. Abstr., vol. 87, No. 11, Abstract No. 116420 (1989).
Magnani et al, Biol. Abstr., vol. 71, No. 11, Abstract No. 74443 (1980).
Roberts et al, Biol. Abstr., vol. 88, No. 4, Abstract No. 38337 (1990).
Deal et al, Biological Abstracts, vol. 90, Abstract No. 100406 (1990).
Physicians' Desk Reference, 40th Edition, Medical Economics Company (Oradell, N.J.), 1986, pp. 612–613, 1288–1289 and 1699.
Lingwood et al, "The Preparation of Rabbit Antiserum Specific for Mammalian Testicular Sulfogalactoglycerolipid", J. Immunol., 124(2): 769–774 (Feb. 1980).
Geary et al, "Identification of Mycoplasma Binding Proteins Utilizing a 100 Kilodalton Lung Fibroblast Receptor", J. Recep. Res. 9(6): 465–478 (1989–90).
Kim, Y. C., "The physicochemical nature of prepared dextran sulfates", Biol. Abstr. 74(3) Abstract No. 19552 (Aug. 1, 1982).
Hofstetter et al, "Production and Characterization of Mouse Antibodies against the Brain Lipid Sulfatide", J. Immunol. Methods, 57:99–109 (1983).
Loomes et al,"Interaction of *Mycoplasma pneumoniae* with Erythrocyte Glycolipids of I and i Antigen Types", Infect. Immun., 47(1):15–20 (Jan. 1985).
Krivan et al, "Adhesion of *Mycoplasma pneumoniae* to (List continued on next page.)

*Primary Examiner*—Toni R. Scheiner
*Assistant Examiner*—Patricia A. Duffy
*Attorney, Agent, or Firm*—Birch, Stewart, Kolasch & Birch

[57] ABSTRACT

A diagnostic kit for detecting the presence of microorganisms, comprising an insoluble substrate; and a carbohydrate receptor immobilized on the insoluble substrate, the carbohydrate receptor being capable of adsorbing microorganisms; and a labelled reagent useful for detecting the presence of microorganisms bound to the carbohydrate receptors and a method for detecting the presence of specified microorganisms in a sample, which comprises contacting a sample to be tested with carbohydrate receptors immobilized on an insoluble substrate; and determining the extent of binding of microorganisms in the sample to the carbohydrate receptors by use of a labelled reagent.

19 Claims, 8 Drawing Sheets

OTHER PUBLICATIONS

Sulfated Glycolipids and Inhibition by Dextran Sulfate", J. Biol. Chem., 264(16):9283–9288 (Jun. 5, 1989).

Roberts et al, "Sialic Acid–dependent Adhesion of *Mycoplasma pneumoniae* to Purified Glycoproteins", J. Biol. Chem., 264(16):9289–9293 (Jun. 5, 1989).

Plosila et al, "Removal of Mycoplasmas from Biological Fluid by Filtration using Mycotrap™, a Receptor Analogue Solid Phase Support", Abstract 0–47, Abstracts of the 92nd General Meeting of ASM, p. 317 (1992).

Krivan et al., Proceeding of the National Academy of Science, USA, vol. 85, No. 1, pp. 6157–6161 (1988).

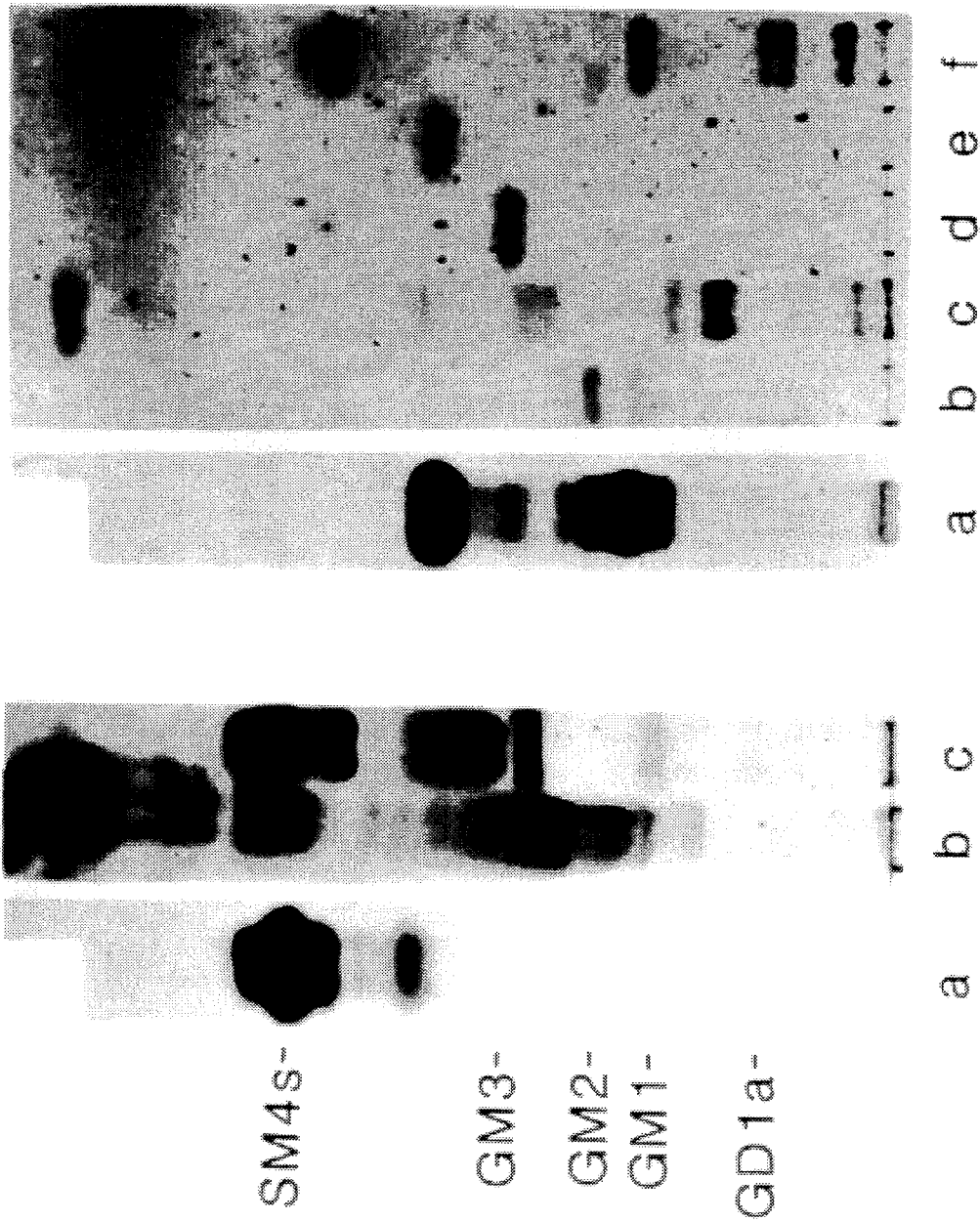

5,529,904

DIAGNOSTIC KIT AND DIAGNOSTIC METHOD FOR MYCOPLASMA UTILIZING CARBOHYDRATE RECEPTORS

CROSS REFERENCE TO RELATED APPLICATIONS

This application is a continuation application of application Ser. No. 07/417,691, filed Oct. 5, 1989, issued as U.S. Pat. No. 5,225,330, which in turn was a continuation-in-part of Ser. No. 07/277,634, filed Nov. 28, 1988, and now issued as U.S. Pat. No. 5,089,479. Ser. No. 07/417,691, was also a continuation-in-part of Ser. No. 07/226,445, filed Aug. 1, 1988 and issued as U.S. Pat. No. 5,217,715.

BACKGROUND OF THE INVENTION

Devices and techniques for the rapid detection of certain bacteria are known in the art. For example, the Tandem Icon Strep A test kit utilizes a procedure wherein *Streptococcus* antigens are extracted from a sample and are bound to a membrane. A colormetric test is then conducted whereby an enzyme conjugated to an antibody is bound to the antigen and thereafter a substrate for the enzyme is contacted with the enzyme. If the enzyme is present, the substrate turns color thereby indicating a positive test. Although this is a useful technique, a need exists for a test having a longer shelf life, which is cheaper and which may be more versatile.

SUMMARY OF THE INVENTION

The present invention is directed to a diagnostic device for adsorbing microorganisms which comprises an insoluble substrate and a carbohydrate receptor capable of adsorbing bacteria bound to the insoluble substrate. The invention also relates to a method for detecting the presence of specified microorganisms in a sample which comprises contacting a sample to be tested with carbohydrate receptors bound to an insoluble substrate and determining the extent of binding of the microorganism in the sample to the carbohydrate receptors bound to the substrate.

Various insoluble substrates to which the carbohydrate receptors can be bound may be used. The substrate should be capable of easily binding the carbohydrate receptors without interfering with the diagnostic test to be conducted. Possible substrates include glass; thin layer chromatographic materials such as silica gel; synthetic plastic materials such as polyvinyl chloride, polystyrene, polypropylene and polyethylene. The substrates may be in the form of flat plates, glass beads, latex beads, thin layers on another substrate, microtiter plates, Petri dishes, etc. The substrate may also be in the form of a membrane or film of either a porous or nonporous nature.

The carbohydrate receptor which is bound to the substrate must bind to the microorganism to be tested. Carbohydrate receptors which selectively bind to various pathogenic gram positive and gram negative bacteria and pathogenic yeast or fungi may be utilized in connection with the present invention. Specifically, it is contemplated that carbohydrate receptors which bind to pathogenic gram positive bacteria such as *Streptococcus* and *Staphylococcus,* pathogenic gram negative bacteria such as *Mycoplasma, Pseuedomonas* and *Escherichia* and pathogenic yeast such as *Cryptococcus* may be utilized in accordance with the present invention.

The term "carbohydrate receptor" means a carbohydrate compound or carbohydrate moiety of a compound which selectively binds to microorganisms. The carbohydrate receptor may have as few as one sugar unit or may have several sugar units.

The monosaccharide unit galactose 3-sulfate contained in sulfatide is an example of a single sugar unit which may function as a carbohydrate receptor. The disaccharide sequence GalNAcβ1- 4Gal may also function as a carbohydrate receptor. The trisaccharide sequence Galβ1-4Glcβ1-1Cer may act as a carbohydrate receptor for *Cryptococcus*. Other structures which may function as carbohydrate receptors include sialyl α(2-3) galactose β(1-4) N-acetylglucosamine for *Mycoplasma pneumoniae*.

The carbohydrate receptor may be part of a glycolipids including sulfated glycolipids such as sulfatide, asialo GM1 and asialo GM2.

Particularly preferred glycolipids are those which contain a terminal Gal(3SO$_4$) β1-residue.

Glycolipids tested for ability to bind various bacteria include the following:

| Name | Structure |
| --- | --- |
| Sulfatide (SO$_4$) | Gal(SO$_4$)β1–1Cer |
| Sulfatide (3SO$_4$) | Gal(3SO$_4$)β1–1Cer |
| Sulfatide (6SO$_4$) | Gal(6SO$_4$)β1–1Cer |
| Lactosylsulfatide | Gal(3SO$_4$)β1–4Glcβ1–1Cer |
| Seminolipid | Gal(3SO$_4$)β1–3alkylacrylglycerol |
| Glucosylceramide (CMH) | Glcβ1–1Cer |
| Lactosylceramide (CDH) | Galβ1–4Glcβ1–1Cer |
| Lacto-N-triaosylcer | GlcNAcβ1–3Galβ1–4Glcβ1–1Cer |
| Paragloboside | Galβ1–4GlcNAcβ1–3Galβ1–4Glcβ1–1Cer |
| α-Galactosylparagloboside | Galα1–3Galβ1–4GlcNAcβ1–3Galβ1–4Glcβ1–1Cer |
| Galactosylceramide (CMH) | Galβ1–1Cer |
| SO$_4$-Glucuronosylparagloboside | GlcA(3SO$_4$) β1–3Galβ1–4GlcNAcβ1–3Galβ1–4Glcβ1–1Cer |
| Trihexosylceramide (CTH) | Galα1–4Galβ1–4Glcβ1–1Cer |
| Asialo GM2 | GalNAcβ1–4Galβ1–4Glcβ1–1Cer |
| Globoside (GL4) | GalNAcβ1–3Galα1–4Galβ1–4Glcβ1–1Cer |
| Asialo GM1 | Galβ1–3GalNacβ1–4Galβ1–4Glcβ1–1Cer |
| GM3 | NeuAcα2–3Galβ1–4Glcβ1–1Cer |
| GM3 (NeuGc) | NeuGcα2–3Galβ1–4Glcβ1–1Cer |
| GM2 | GalNAcβ1–4[NeuAcα2–3]Galβ1–4Glcβ1–1Cer |
| GM1 | Galβ1–3GalNAcβ1–4[NeuAcα2–3]Galβ1–4Glcβ1–1Cer |
| Sialylparagloboside | NeuAcα2–3Galβ1–4GlcNAcβ1–3Galβ1–4Glcβ1–1Cer |

-continued

| Name | Structure |
|---|---|
| Sialylparagloboside (NeuGc) | NeuGcα2–3Galβ1–4GlcNAcβ1–3Galβ1–4Glcβ1–1Cer |
| Sialylneolactofuco-pentaosylcer | NeuAcα2–3Galβ1–4[Fucα1–3]GlcNAcβ1–3Galβ1–4Glcβ1–1Cer |
| GD1a | NeuAcα2–3Galβ1–3GalNAcβ1–4[NeuAcα2–3]–Galβ1–4Glcβ1–1Cer |
| GD1b | Galβ1–3GalNAcβ1–4[NeuAcα2–8Neuα2–3]Galβ1–4Glcβ1–1Cer |
| GT1b | NeuAcα2–3Galβ1–3GalNacβ1–4[NeuAcα2–8NeuAcα2–3]Galβ1–4Glcβ1–1Cer |
| Sialylneolacto-hexasolycer | NeuGcα2–3Galβ1–4GlcNAcβ1–3Galβ1–4GlcNAcβ1–3Galβ1–4Glcβ1–1Cer |
| Fucosylasialo–GM1 | Fucα1–2Galβ1–3GalNAcβ1–4Galβ1–4Glcβ1–1Cer |
| Asialo-Cad | GalNAcβ1–4Galβ1–4GlcNAcβ1–3Galβ1–4Glcβ1–1Cer |
| Forssman | GalNAcα1–3GalNAcβ1–3Galα1–4Galβ1–4Glcβ1–1Cer |
| Cad | GalNAcβ1–4(NeuAcα2–3)Galβ1–4GlcNAcβ1–3Galβ1–4Glcβ1–1Cer<br>Galα1–3Galβ1–4GlcNAcβ1 |
| I-Active Sialyl-lactoisooctaosylcer | ⁶Galβ1–4GlcNAcβ1–3Galβ1–4Glcβ1–1Cer<br>NeuAcα2–3Galβ1–4GlcNAcβ1 3<br>Galβ1–4GlcNAcβ1 6 |
| I-active Lacto-isooctaosylcer | Galβ1–4GlcNAcβ1–3Galβ1–4Glcβ1–1Cer<br>Galβ1–4GlcNAcβ1 ³<br>Galα1–3Galβ1–4GlcNAcβ1 |
| I-active Gal₂-lactoisooctaosylcer | ⁶Galβ1–4GlcNAcβ1–3Galβ1–4Glcβ1–1Cer<br>Galα1–3Galβ1–4GlcNAcβ1 3 |

Trivial names and structures are represented according to recommendations in IUPAC-IUB Joint Commission on Biochemical Nomenclature, Eur. J. Biochem., 159, 1–6 (1986) and references cited therein; cer, ceramide.

Glycolipids which binds to *Escherichia coli* include:

| Name | Structure |
|---|---|
| N-glycolyl-GM3 | NeuGcα2–3Galβ1–4Glcβ1–1Cer |
| N-glycolylsialopara-globoside | NeuGcα2–3Galβ1–4GlcNAcβ1–3Galβ1–4Glcβ1–1Cer |

The binding of these two glycolipids to *Escherichia coli* is described by Kyogashima et al, Archives of Biochemistry and Biophysics, 270, No. 1, 391–397 (April 1989) which is hereby incorporated by reference.

The carbohydrate receptor may be part of a glycoprotein such as laminin, fetuin, human chorionic gonadotropin, human platelet thrombospondin and derivatives of these glycoproteins. Particularly preferred glycoproteins are those with α2-3-linked sialic acid.

The glycolipid lactosylceramide which has the structure Galβ1-4Glcβ1-1Cer binds to the yeastlike fungus *Cryptococcus neoformans*.

The carbohydrate receptor should be bound to the substrate in an amount sufficient to and in a manner which allows binding of the bacteria to be diagnosed to the carbohydrate receptor. From a practical point of view, the carbohydrate receptor will usually be present in an amount of at least 0.1 pmol/mm$^2$, more preferably at least 1 pmol/mm$^2$ of surface area of the substrate. As far as the upper limit of the concentration of the carbohydrate receptor on the substrate, the carbohydrate receptor can be bound up to the saturation density of the substrate. The saturation density of sulfatide on polystyrene is about 3 pmol/mm$^2$. The carbohydrate receptor can be bound as a molecular monolayer which substantially completely covers the surface area of the substrate. Use of more than a molecular monolayer of carbohydrate receptors bound to the substrate may result in a waste of materials and may result in inefficient binding of the carbohydrate receptor to the substrate. A preferred range for the density of the carbohydrate receptor bound to the substrate is 0.1 pmol/mm$^2$ to the saturation density of the carbohydrate receptor, more preferably 0.1 to 3 pmol/mm$^2$.

The actual concentration of carbohydrate receptor bound to a given substrate will depend upon the particular bacteria to be diagnosed and the binding efficiency of the carbohydrate receptor to the particular bacteria.

The carbohydrate receptor may be bound to the substrate in any suitable manner. Covalent or non-covalent (e.g., hydrophobic) bonding may be used to bind the carbohydrate receptor to a substrate. For example, the lipid portion of glycolipids will hydrophobically bond to certain plastic substrates leaving the carbohydrate receptor, i.e., the sugar or glyco group, the available to bind to microorganisms. Alternatively, a carbohydrate receptor may be covalently bonded to a substrate. Other forms of bonding such as ionic bonding may be used.

The carbohydrate receptor may also be bound to particles, such as latex particles, which are thereafter immobilized on by imbedding in or binding to a porous membrane. The latex particles may be of a size which can be embedded by pressure into the pores of the porous membrane. Thus, for example, the average particle size of the latex particles may be about the same as, or slightly smaller than, the average surface pore size of said porous membrane. Alternatively, the particles may be bound to any porous or liquid permeable material such as a screen, net, etc. A material such as a binder may be used to bind the particles to the support as long as the binder does not interfere with the ability of the carbohydrate receptors to bind microorganisms. In another embodiment, the particles may be packed in a container such as a column having an inlet and an outlet, whereby the sample to be tested and the necessary diagnostic reagents may be contacted with the particles when passing through the container.

Various samples can be tested for the presence of bacteria by the method of the present invention. For diagnosis of disease and/or infections a body sample from a patient suspected of being infected will normally be diluted in an appropriate solution such as physiological saline and this solution will then be contacted with the diagnostic device containing the substrate and the carbohydrate receptors. When testing for the presence of pathogens in the oral cavity of a patient to be tested, a cotton swab or other material will be swabbed in the inside of the patient's mouth and this swab will be placed in a sterile solution whereby bacteria in the cotton swab will be released from the swab into the solution. This solution will then be tested for the presence of bacteria. It is also possible to test for bacteria in body fluids such as sputum, urine, saliva and blood.

The present invention may also be utilized to test for other types of bacteria such as bacteria which may contaminate environments which should be kept sterile such as hospital operating rooms, drug and medical device manufacturing facilities, food manufacturing facilities, etc. In such situations, the area to be tested will usually be swabbed and the swab will be placed into a sterile solution to release the bacteria in much the same manner as when a swab sample is taken from a patient's mouth. This solution can then be contacted with the device of the present invention.

The solution suspected of containing bacteria is contacted with the substrate containing the carbohydrate receptors described hereinabove. Preferably, the solution is contacted with the substrate until or before equilibrium is reached, e.g., 1 to 90 minutes, more preferably 5 to 60 minutes at a temperature of 0° to 40° C., preferably 4° to 37° C., depending on the microorganism to be tested. For example, the preferred temperature for *Mycoplasma* appears to be about 37° C. whereas the preferred temperature for *Clostridium* appears to be about 4° C. The precise time and temperature conditions are selected to provide sufficient time for the bacteria to adsorb to the carbohydrate receptors to a degree sufficient to allow for accurate testing. The sample to be tested may be dissolved and/or diluted with various liquids such as physiological saline, etc.

After the solution has been contacted with the substrate containing the carbohydrate receptors for a time sufficient to allow the bacteria to bind to the carbohydrate receptors, the substrate is washed to remove all unbound materials.

A test is then conducted to determine the presence of the bacteria bound to the carbohydrate receptors on the substrate. Various tests to accomplish this purpose are known in the art such as the enzyme linked immunosorbent assay (ELISA), a radioimmune assay test, direct or indirect fluorescent antibody test, etc. Basically, the substrate containing the carbohydrate receptors and suspected of containing bacteria bound thereto is contacted with a material which binds to the bacteria to be tested. Such materials include, for example, antibodies against the bacteria or a carbohydrate receptor which binds to the bacteria.

The antibody or carbohydrate receptor may be "labelled" with a substance which may be easily detected. For example, the antibody or carbohydrate receptor may be conjugated with an enzyme, radioactive material or element or fluorescent material. If the antibody or carbohydrate receptor is conjugated with an enzyme, the substrate is thereafter contacted with a substrate for the enzyme which preferably turns color upon contact with the enzyme thereby indicating a positive reaction. The antibody or carbohydrate receptor to be used should be one which reacts with the bacteria but which does not react with the coated substrate or with the carbohydrate receptors bound to the substrate thereby preventing a false positive reading. If the enzyme or carbohydrate receptor is radioactively labelled, then the presence of radioactivity on the substrate should be measured. It is also possible that the enzyme or carbohydrate receptor may be fluorescently labelled. In this situation the treated substrate should be exposed to ultraviolet light to determine the presence of the fluorescent labelled material bound to the substrate.

Alternatively, the test may include the following steps:

(I) providing a carbohydrate receptor on a substrate to provide a coated surface on said substrate;

(II) contacting a patient's bodily fluids or tissue extracts with said coated substrate surface to selectively bind microorganisms in said patient's bodily fluids or tissue extracts to said coated surface;

(III) contacting, after step (II), a first antibody against said microorganism with said coated surface, to bind said second antibody to said coated surface when said microorganism has previously bound to said coated surface in step II;

(IV) contacting, after step III, an enzyme labeled antibody which is reacted with said first antibody with said coated surface, to bind said enzyme labeled antibody to said coated surface when said first antibody has previously bound to said coated surface in step III; and (V) contacting, after step IV, said coated substrate with a chemical (enzyme label indicator) which indicates the presence of said enzyme labeled antibody bound to said coated surface.

BRIEF DESCRIPTION OF THE DRAWINGS

FIG. 5. Identification of sulfatide synthesized by WiDr adenocarcinoma cells. WiDr cells were metabolically labeled with [$^{35}$S]-sulfate as described in Materials and Methods. Neutral acidic lipids were chromatographed on silica gel high performance thin layer plates developed in chloroform/methanol/0.25% KCl in water, 5:4:1 (Panel A) or chloroform/methanol/acetone/acetic acid/water, 8:2:4:2:1 (Panel B). The lipids were detected by autoradiography (lane a) or orcinol reagent (lanes b–f). Panel A, [$^{35}$S]-labeled acidic lipids from $10^6$ WiDr cells (lane a), neutral (lane b) and acidic (lane c) lipids from 30 mg wet weight of WiDr cells. The orcinol positive sulfatide band is indicated by the arrow (←). Migration of reference glycolipids is indicated in the left margin: sulfatide, GM3, GM2, GM1, GD1a, GD1b, and GT1b. Panel B, [$^{35}$S]-labeled acidic lipids from $10^6$ WiDr cells (lanes a & c), bovine brain sulfatide (land b), seminolipid (lane d), cholesterol 3-sulfatide (lane e), and neutral glycolipid standards from top to bottom CMH, CDH, CTH, and GL4 (lane f). For abbreviations, see footnote 1 and Table I.

DETAILED DESCRIPTION OF THE INVENTION

Figure 1A:
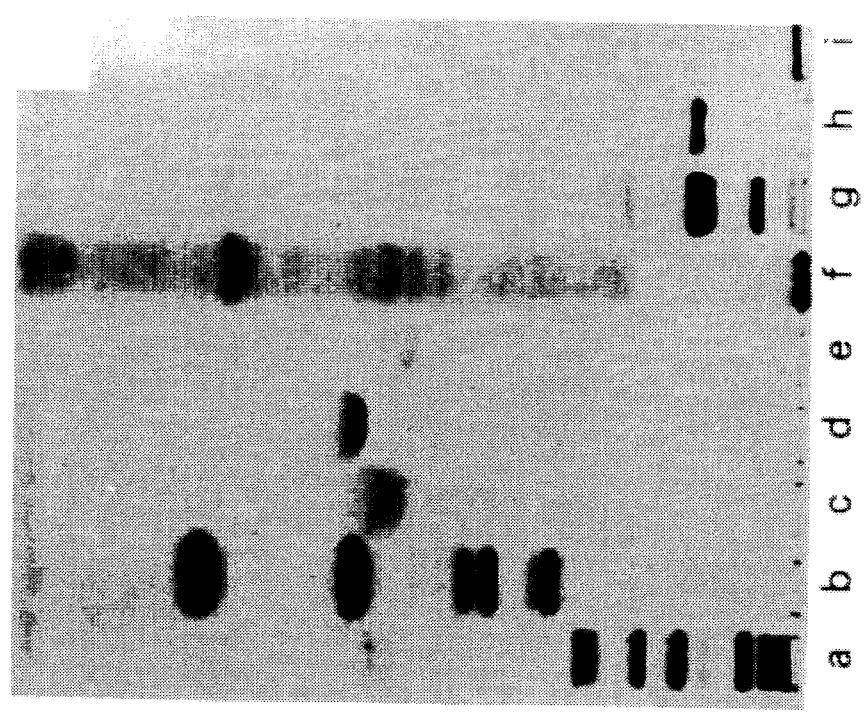
FIG. 1. Binding of *M. pneumoniae* to glycolipids separated by thin layer chromatography. Glycolipids were chromatographed on aluminum-backed silica get HPTLC plates developed in chloroform/methanol/0.25% $CaCl_2$ in water, 60:35:8. The plates were coated with plastic, soaked in Tris-BSA, and incubated for 3 h at 25° C. with [$^3$H]-palmitate-labeled *M. pneumoniae* suspended in RPMI 1640 containing 1% BSA and 25 mM HEPES, pH 7.3, as described in Materials and Methods (Panel A), or sprayed with orcinol reagent to identify glycolipids (Panel B). Lane a, acidic glycolipid standards sulfatide (0.5 μg), GM3 (2 μg), GM2 (2 μg), GD1a (2 μg), GD1b (2 μg), GT1b (2 μg); lane b, neutral standards galactosyl ceramide (4 μg), lactosylceramide (4 μg), globotriaosylceramide (2 μg), and globotetraosylceramide (2 μg); lanes c and $c_1$, sulfatide (2 μg), $c_2$ (0.5 μg), and $c_3$ (0.1 μg); lane d, seminolipid (2 μg); lane e, cholesterol 3-sulfate (2 μg); lane f, human trachea acidic glycolipids from 100 mg wet weight of tissue; lane g, monosialoganglioside from 100 mg wet weight of bovine erythrocytes; lane h, α2-3sialylparagloboside (2 μg); lane i, I-active monosialylganglioside from bovine erythrocytes (2 μg). For abbreviations, see footnote 1 and Table I.

The term "antibody" as used herein refers to polyclonal antibodies or monoclonal antibodies. Although polyclonal antibodies are preferred, monoclonal antibodies having appropriate binding ability to the desired "antigens" may be substituted therefor.

The term "bodily fluid" refers to any human liquid product as for example sputum, saliva, plasma, peritoneal fluid, cerebrospinal fluid and so forth.

The term "enzyme labelled antibody" as used herein refers to an antibody labelled with an enzyme such as alkaline phosphatase, peroxidase, or the like, which is capable of reaction with a chemical indicator as defined below.

The term "enzyme label indicator" as used herein refers to chemical indicators for indicating, preferably by color change, the presence of enzyme labelled antibody bound to the substrate's coated surface. For example, p-nitrophenol phosphate is one such enzyme label indicator for the enzyme alkaline phosphatase.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

EXAMPLE 1

Materials—Dextran sulfate ($M_r$ 500,000, lot 44F-0408 and $M_r$ 5,000, lot 77F-0634), fucoidin, colominic acid (*E. coli*), hyaluronate, dipalmitoylphosphatidylcholine (synthetic), cholesterol (Grade I, 99%), cholesterol 3-sulfate, and bovine serum albumin (A7030 fatty acid and globulin free), were from Sigma. Bovine lung heparin (160 units/mg) was from the UpJohn Co. RPMI 1640 medium was purchased from Biofluids.

Glycolipids—Bovine brain sulfatide (galactosyl ceramide-I$^3$-sulfate), ceramide monohexoside, ceramide trihexoside, globoside, and gangliosides GM1 and GD1a were obtained from Supelco. Lactosylceramide and glucosylceramide were from Calbiochem. Other reference gangliosides were from Bachem, Inc. Seminolipid (β-galactosylalkylacylglycerol-I$^3$ -sulfate) was isolated from bovine testes (Pel-Freez Biologicals) as previously described (Roberts, D. D., Wewer, U. M., Liotta, L. A., and Ginsburg, V., *Cancer Res.*, 48, 3367–3373 (1988)). Galactosyl ceramide-I$^6$-sulfate was prepared as previously described by sulfation of galactosyl ceramide (Roberts, D. D., Rao, C. N., Liotta, L. A., Gralnick, H. R., and Ginsburg, V., *J. Biol. Chem.*, 261, 6872–6877 (1986)). Sulfated glucuronosylparagloboside (IV$^3$-[3'SO$_3$GlcA]-nLcOse$_4$Cer) was purified from human peripheral nerve (Chou, D. K. H., Ilyas, A. A., Evans, J. E., Costello, C., Quarles, R. H., and Jungalwala, F. B., *J. Biol. Chem.*, 261, 11717–11725 (1986)). Lactosylceramide-II$^3$-sulfate, GM3, and sialyllactofucopentaosyl-(III)-ceramide were purified from human kidney (Martensson, E., *Biochim. Biophys. Acta*, 116, 521–531 (1966); Rauvala, H., *J. Biol.*

Chem., 251, 7517–7520 (1976); Hanfland, P., Egge, H., Dabrowski, U., Kuhn, S., Roelche, D. and Dabrowski, J., Biochemistry, 20, 5310–5319 (1981)). α-Galactosylparagloboside (IV$^3$GalnLcOse$_4$Cer) and the I-active α-Gal$_2$lactoisooctaosylceramide were purified from rabbit erythrocytes (Pel-Freez) (Watanabe, K., Hakomori, S., Childs, R. A., and Feizi, T., J. Biol. Chem., 254, 3221–3228 (1979)). Lactoisooctaosylceramide was prepared from the latter lipid by treatment with coffee bean α-galactosidase. α2-3-Sialylparagloboside (NeuGc), α2-3-sialyllactoneohexaosylceramide, GM3 (NeuGc), and an I-active ganglioside were prepared from bovine erythrocytes (Watanabe, K., Powell, M. E., and Hakomori, S., J. Biol. Chem., 254, 8223–8228 (1979)). α2-3-Sialylparagloboside (NeuAc) was isolated from type O human erythrocytes (Ando, S., Kon, K., Isobe, M., Nagai, Y., and Yamakawa, T., J. Biochem., 79, 625–632 (1976)). Paragloboside and lactoneohexaosylceramide were prepared by desialylation of the respective gangliosides with 1M formic acid for 60 min. at 100° C. Asialo-GM1 and asialo-GM2 were prepared as previously described (Krivan, H. C., Roberts, D. D., and Ginsburg, V., Proc. Natl. Acad. Sci., 85, 6157–6161 (1988)). Lacto-N-triaosylceramide was prepared by digestion of paragloboside with bovine testes β-galactosidase (Boehringer Mannheim). The identities of the neolacto-series glycolipids was confirmed by immunostaining with monoclonal antibody My-28 before and after neuraminidase digestion (Spitalnik, S. L., Schwartz, J. F., Magnani, J. L., Roberts, D. D., Spitalnik, P. F., Civin, C. I., and Ginsburg, V., Blood, 66, 319–326 (1985)). Concentrations of galactosyl ceramide I$^6$-sulfate, galactosyl ceramide I$^3$-sulfate, cholesterol sulfate, glucosylceramide, galactosylceramide, lactosylceramide, asialo-GM1, and asialo-GM2 were determined by dry weight. Other sulfated glycolipids were determined by the dye-binding assay of Kean (Kean, E. L., J. Lipid Res., 9, 319–327 (1968)) as modified by Tadano-Aritomi and Ishizuka (Tadano-Aritomi, K., and Ishizuka, I., J. Lipid Res., 24, 1368–1375 (1983)). The concentrations of the other neutral and acidic glycolipids listed in Table I were determined by densitometry (QuickScan, Helena Laboratories) of orcinol-stained thin-layer chromatograms compared with authentic standards. The purity of all lipids were confirmed by thin-layer chromatography in neutral and acidic solvent systems.

Lipids were extracted from normal human lung, trachea, and WiDr cells (Krivan, H. C., Roberts, D. D., and Ginsburg, V., Proc. Natl. Acad. Sci., 85, 6157–6161 (1988); Svennerholm, L. and Fredman, P., Biochim. Biophys. Acta, 617, 97–109 (1980)) and separated into neutral and acidic fractions by anion exchange chromatography on DEAE-Sepharose in the biocarbonate form. For some experiments, WiDr cells were metabolically labeled with [$^{35}$S]-sulfate (ICN Radiochemicals). Labeling was done for 48 h in Hams F12 medium with 10% fetal calf serum, 10% RPMI 1640, and 100 μCi/ml [$^{35}$S]-sulfate (total sulfate concentration 80 μM). Equilibration of [$^{35}$S]-sulfate with the intracellular pool in WiDr cells is complete within 4 hours (Iozzo, R. V., J. Cell. Biol., 99, 403–417 (1984)). The carrier sulfate concentration was selected to minimize dilution of the intracellular sulfate pool by metabolism of sulfur-containing amino acids and under sulfation due to low carrier sulfate concentrations (Iozzo, R. V., J. Biol. Chem., 262, 1888–1900 (1987); Humphries, D. E., Silbert, C. K., and Silbert, J. E., Biochem. J., 252, 305–308 (1988)). Thus, the specific activity of the incorporated sulfate under these conditions should equal that in the medium. Cells were removed from the tissue culture flasks by removing the medium and adding 2.5 mM EDTA in 10 mM phosphate buffered saline, pH 7.3. After 60 min at 37° C., the cells were collected by centrifugation and extracted as described above. Desalted lipid extracts were analyzed by high performance thin layer chromatography developed in chloroform:methanol:0.25% KCl in water (5:4:1) or chloroform:methanol:acetone:acetic acid:water (8:2:4:2:1). The labeled sulfated glycolipids were visualized by autoradiography and quantified by scraping the bands and scintillation counting. Sulfated glycolipids in the tissue extracts were detected by staining of the lipids separated by high performance thin layer chromatography with $^{125}$I-von Willebrand factor (Roberts, D. D., Williams, S. B., Gralnick, H. R., and Ginsburg, V., J. Biol. Chem., 261, 3306–3309 (1986)).

Growth and Labeling of Organisms—Virulent M. pneumoniae strain M129, passage 4–6, were grown and metabolically labeled with [$^3$H]palmitic acid (12–17 Ci/mmole, New England Nuclear Corp., Boston) as previously described (Chandler, D. K. F., Collier, A. M. and Barile, M. F., Infect. Immun., 37–942 (1982)). The organisms were passed four times through a 26 gauge needle and suspended to approximately $10^7$ cpm/ml of degassed RPMI 1640 medium containing 1% bovine serum albumin (Sigma, fatty acid free) and 25 mM Hepes, pH 7.3 (RPMI-BSA).

Mycoplasma Overlay Assay—M. pneumoniae were bound to glycolipids separated on thin-layer chromatograms as described in detail for other bacteria (Krivan, H. C., Roberts, D. D., and Ginsburg, V., Proc. Natl. Acad. Sci., 85, 6157–6161 (1988); Krivan, H. C., Ginsburg, V. and Roberts, D. D., Arch. Biochem. Biophys., 260, 493–496 (1988)). Briefly, glycolipids were separated by thin-layer chromatography on aluminum-backed silica gel high-performance plates (Merck, West Germany) developed with chloroform:methanol: 0.25% CaCl$_2$ in water (60:35:8). After chromatography, the plates were coated with 0.1% polyisobutylmethacrylate, soaked in 0.05M Tris-HCl, pH 7.6, containing 110 mM sodium chloride, 5 mM CaCl$_2$, 0.2 mM phenylmethane-sulfonyl fluoride, and 1% bovine serum albumin (TBS-BSA) and incubated for 3 h at 25° C. with 60 μl/cm$^2$ of [$^3$H]-labeled M. pneumoniae (approximately $10^7$ cpm/ml of RPMI-BSA). The plates were gently washed five times in 0.01M sodium phosphate, pH 7.2, containing 0.15M sodium chloride (PBS) to remove unbound organisms, dried, and exposed for 24 h to Ultrofilm $^3$H (2208-190) high speed film (LKB).

Figure 1B:
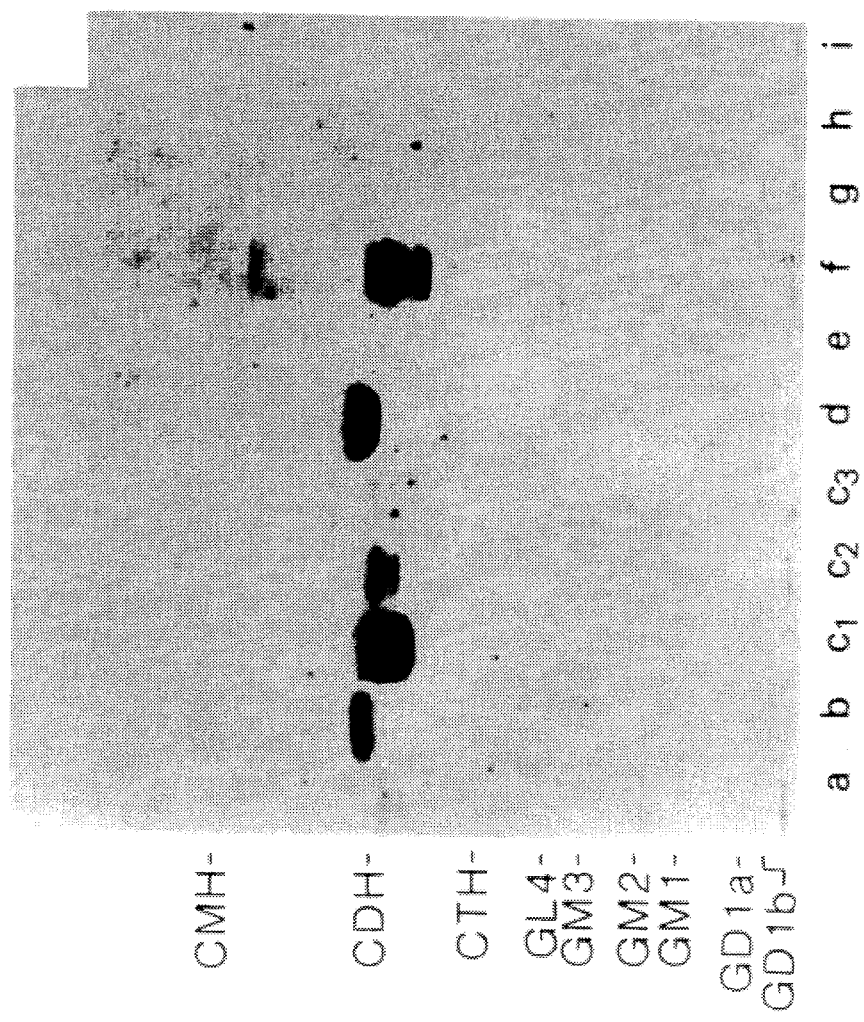

Glycolipids were chromatographed on aluminum-backed silica gel HPTLC plates developed in chloroform/methanol/ 0.25% CaCl$_2$ in water, 60:35:8. The plates were coated with plastic, soaked in Tris-BSA, and incubated for 3 h at 25° C. with [$^3$H]-palmitate-labeled M. pneumoniae suspended in RPMI 1640 containing 1% BSA and 25 mM HEPES, pH 7.3, as described in Materials and Methods (Panel A), or sprayed with orcinol reagent to identify glycolipids (Panel B). The results are shown in FIG. 1. Lane a, acidic glycolipid standards sulfatide (0.5 μg), GM3 (2 μg), GM2 (2 μg) GD1a (2 μg), GD1b (2 μg), GT1b (2 μg); lane b, neutral standards galactosyl ceramide (4 μg), lactosylceramide (4 μg), globotriaosylceramide (2 μg), and globotetraosylceramide (2 μg); lanes c and c$_1$, sulfatide (2 μg), c$_2$ (0.5 μg) and c$_3$ (0.1 μg); lane d, seminolipid (2 μg); lane e, cholesterol 3-sulfate (2 μg); lane f, human trachea acidic glycolipids from 100 mg wet weight of tissue; lane g, monosialoganglioside from 100 mg wet weight of bovine erythrocytes; lane h, α2-3sialylparagloboside (2 μg); lane i, I-active monosialylganglioside from bovine erythrocytes (2 μg). For abbreviations see footnote 1 and Table I. The results for glycolipids tested for ability to bind *M. pneumoniae* are shown in Table I.

TABLE I

| Name | Binding* |
| --- | --- |
| Sulfatide (3SO$_4$) | +++ |
| Sulfatide (6SO$_4$) | +++ |
| Lactosylsulfatide | +++ |
| Seminolipid | +++ |
| Glucosylcer (CMH) | + |
| Lactosylcer (CDH) | ++ |
| Lacto-N-triaosylcer | + |
| Paragloboside | + |
| α-Galactosylparagloboside | + |
| Galactosylcer (CMH) | – |
| SO$_4$-Glucuronosylparagloboside | – |
| Trihexosylcer (CTH) | – |
| Asialo GM2 | – |
| Globoside (GL4) | – |
| Asialo GM1 | – |
| GM3 | – |
| GM3 (NeuGc) | – |
| GM2 | – |
| GM1 | – |
| Sialylparagloboside | – |
| Sialylparagloboside (NeuGc) | – |
| Sialylneolactofucopentaosylcer | – |
| GD1a | – |
| GD1b | – |
| GT1b | – |
| Sialylneolactohexaosylcer | – |
| I-Active Sialyllactoisooctaosylcer | – |
| I-active Lactoisooctaosylcer | – |
| I-active Gal$_2$-lactoisooctaosylcer | – |

*Negative binding (–) indicates no binding to 4 μg of lipid and positive binding to less than 0.5 μg (+++), 0.5 to 2 μg (++), and 2–4 μg (+).

Solid-Phase Binding Assay—The binding of *M. pneumoniae* to purified glycolipids immobilized in microtiter plates (Falcon 3912, Becton Dickinson) was measured as previously described (Krivan, H. C., Ginsburg, V. and Roberts, D. D., *Arch. Biochem. Biophys.*, 260, 493–496 (1988)). Purified glycolipids were serially diluted in 25 μl of methanol containing 0.1 μg each of the auxiliary lipids cholesterol and phosphatidylcholine. After the solutions were dried by evaporation, the wells were filled with TBS-BSA, emptied after 1 h, rinsed with RPMI-BSA, and incubated with 25 μl of [$^3$H]-*M. pneumoniae* (approximately 10$^7$ cpm/ml RPMI-BSA). After incubation for 2 h at 37° C. (unless otherwise stated), the wells were washed five times with saline and bound *M. pneumoniae* was quantified by scintillation counting in Aquasol. For inhibition studies, various polysaccharides were serially diluted in 25 μl of RPMI-BSA in microtiter wells followed by the addition of 25 μl of [$^3$H]-*M. pneumoniae*.

Mycoplasma adhesion to cultured cells—Adhesion of [$^3$H] -*M. pneumoniae* to cells on glass covered slips was measured by a modification of a method previously described (Chandler, D. K. F., Collier, A. M., and Barile, M. F., *Infect. Immun.*, 37–942 (1982)). WiDr human colon adenocarcinoma (ATCC CCL 218) was grown in Eagle's minimal essential medium with 10% fetal calf serum (Biofluids) in a 5% CO$_2$ atmosphere at 37° C. The cells were removed with trypsin and plated on 12 mm round glass coverslips in 24-well tissue culture plates and grown for 3 days. Control coverslips were preincubated in medium without cells. The coverslips were washed in serum-free medium then incubated in RPMI-BSA for 15 min. The medium was removed and labeled *M. pneumoniae* suspended in 0.5 ml of RPMI-BSA were added to each well. The plates were incubated on a rocking table for 60 min, at 37° C. The coverslips were washed by dipping in saline six times and the bound radioactive bacteria determined by scintillation counting. For inhibition studies, the inhibitors were added to *M. pneumoniae* prior to adding the bacteria to the coverslips.

RESULTS

Binding of *M. pneumoniae* to Glycolipids on Thin Layer Chromatograms—Incubation of [$^3$H]-labeled *M. pneumoniae* with various glycolipids resolved on thin layer chromatograms was used to determine the carbohydrate binding specificity of the organism. As shown by an autoradiogram (FIG. 1A) compared with a similar thin layer plate visualized with orcinol reagent (FIG. 1B), *M. pneumoniae* bound avidly to authentic sulfatide, detecting 100 ng of this glycolipid (lane c$_3$), and to a glycolipid with the same mobility as sulfatide in the acidic lipid fraction of human trachea (land f). This tracheal glycolipid was confirmed to be sulfatide by its specific staining with $^{125}$I-labeled von Willebrand factor (Roberts, D. D., Williams, S. B., Gralnick, H. R. and Ginsburg, V., *J. Biol. Chem.*, 261, 3306–3309 (1986)). Sulfatide was also detected in human lung lipids but at lower levels than in trachea. *M. pneumoniae* also bound to other sulfated glycolipids including lactosyl sulfatide and seminolipid, which contain the same terminal Gal(3SO$_4$)β1-residue as sulfatide, and an isomer of sulfatide in which the terminal sulfate is linked to the 6-position of galacross. Interestingly, *M. pneumoniae* also binds to high amounts of lactosylceramide and to a lesser extent glucosylceramide, paragloboside, lactotriaosylceramideande-galactosylparagloboside, but not to other neutral glycolipids (Table I). No binding was detected to other acidic glycolipids including α2-3-sialylparagloboside, I-active monosialylganglioside, or to the gangliosides GM3, GM2, GM1, GD1a, GD1b, and GT1b. In addition, sulfate itself is not sufficient for binding as *M. pneumoniae* does not bind to high amounts of cholesterol sulfate or to sulfated glucuronosylparagloboside, which has a terminal sulfate linked to the 3-position of glucuronic acid.

Figure 2:
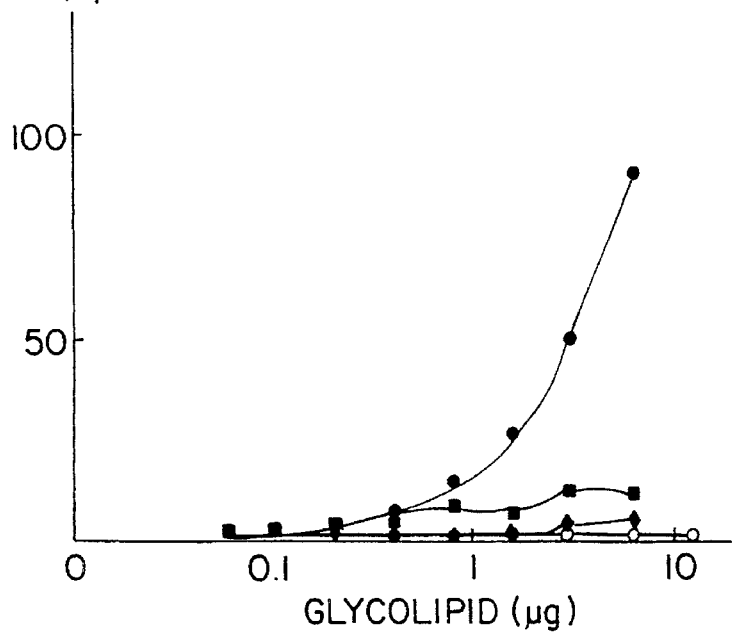
FIG. 2. Binding of *M. pneumoniae* to purified glycolipids. Lipids in 25 μl of methanol containing 0.1 μg each of the auxiliary lipids cholesterol and phosphatidylcholine were evaporated in flat bottom wells of polyvinylchloride microtiter plates. The wells were blocked with 1% albumin for 1 h, washed twice with RPMI-BSA, and incubated at 25° C. with 25 μl of [$^3$H]-*M. pneumoniae* (approximately $10^5$ cpm). After 2 h, the wells were washed five times with saline, cut from the plate, and bound radioactivity quantified in a scintillation counter. In cotnrol experiments organisms were incubated with auxiliary lipids only to correct for nonspecific binding (typically <1% of the total radioactivity added). *M. pneumoniae* binding was determined in RPMI-BSA for sulfatide (solid circles), lactosylceramide (solid squares), paragloboside (solid diamonds), and cholesterol sulfate, ceramide trihexoside, globoside, GM1, GM2, or GM3 (open circles).
Figure 3:
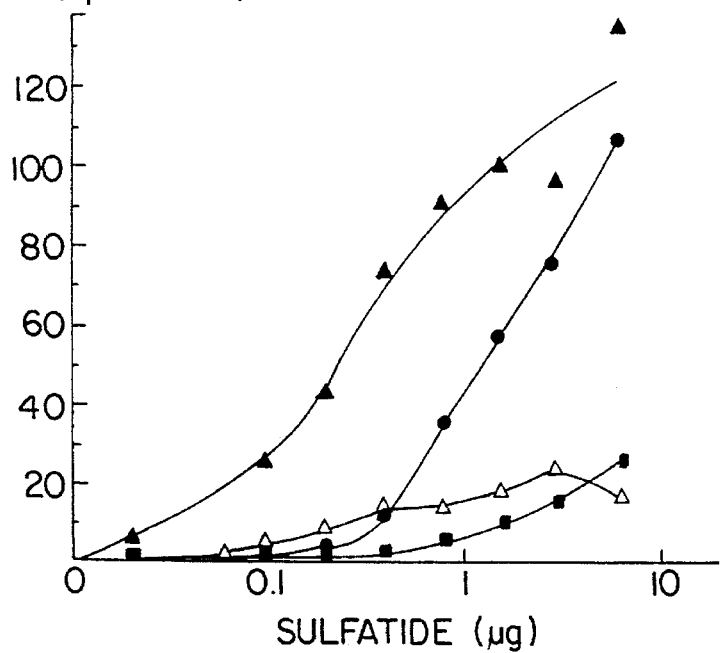
FIG. 3. Energy and temperature dependent binding of *M. pneumoniae* to sulfatide. Microtiter wells were coated with sulfatide and blocked with albumin as described in the legend of FIG. 2. Binding of [$^3$H]-*M. pneumoniae* was determined in RPMI-BSA for 2 h at 4° C. (solid square), 25° C. (solid circle), 37° C. (solid triangle), and at 37° C. in BSA without RPMI (open triangle).
Figure 4:
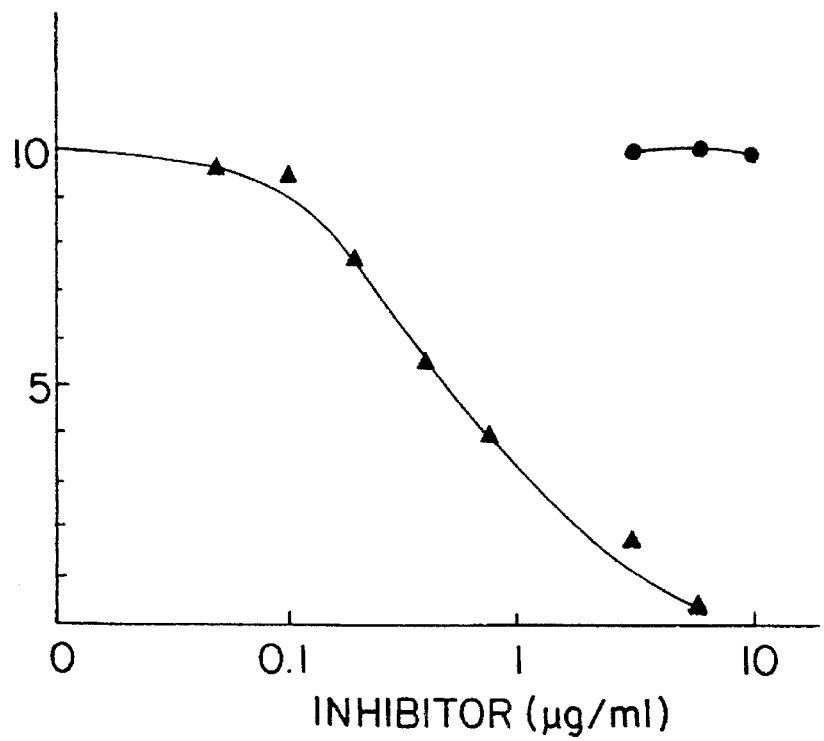
FIG. 4. Inhibition of *M. pneumoniae* binding to sulfatide by dextran sulfate. Polysaccharides were serially diluted with 25 μl of RPMI-BSA in microtiter wells previously coated with 1 μg of purified sulfatide. Binding was determined after incubation for 2 h at 37° C. with 25 μl of [$^3$H]-*M. pneumoniae* with the indicated concentration of dextran (solid circle) or dextran sulfate (solid triangle).

Quantitative Binding of *M. pneumoniae* to Immobilized Glycolipids in Microtiter Plates—Binding of *M. pneumoniae* to purified glycolipids adsorbed on microtiter plates was examined to further define binding specificity. Binding to sulfatide was sensitive and dose-dependent (See FIG. 2). *M. pneumoniae* bound weakly to lactosylceramide and paragloboside, whereas no binding was detected to cholesterol sulfate or other glycolipids tested at 10 μg per well, consistent with the data obtained from the overlay assay. Binding of *M. pneumoniae* to sulfatide is both energy and temperature dependent (See FIG. 3). At 37° C. about 0.25 μg of sulfatide was required for half-maximum binding. The binding activity was about 5 times lower at 25° C. and was minimal at 4° C. *M. pneumoniae* also bound poorly at 37° C. in nutrient-deficient medium (Tris-BSA without RPMI) with binding activities comparable to that obtained at 4° C. (FIG. 3). These results suggest that *M. pneumoniae* requires energy and physiological temperatures for maximal binding to occur.

EXAMPLE 2

MATERIALS

Laminin purified from the mouse Engelbreth Holm Swarm tumor was provided by Dr. Lance Liotta, NCI, NIH. Thrombospondin was purified from thrombin-stimulated human platelets (Roberts, D. D., Haverstick, D. M., Dixit, V. M., Frazier, W. A., Santoro, S. A. and Ginsburg, V., *J. Biol. Chem.*, 260, 9405–9411 (1985)). Human plasma fibronectin was from Collaborative Research, Inc. Human chorionic gonadotropin (hCG)[1] and the purified alpha subunit were provided by Drs. Bruce Weintraub and Peter Gyves, NIDDK, NIH. Most other proteins, dextran sulfate Mr 500,000, and neuraminidase (*Chlostridium perfringens*, Type VI) were obtained from Sigma.

6'-Sialyllactose from human milk was provided by Dr. David Smith, Department of Biochemistry and Nutrition, Virginia Polytechnic Institute and State University. 3'Sialyllactose was isolated from human milk or from a mixture of sialyllactose isomers from bovine colostrum (Boehringer Mannheim Biochemicals), Contamination of the 6'-sialyllactose with 3'-sialyllactose was less than 2% as determined by anion exchange chromatography on an AS-6 column (Dionex Corp., Sunnyvale, Calif.).

Oligosaccharides from 500 mg of bovine fetuin (Sigma) were released by digestion in 0.2M sodium phosphate, pH 8.6, containing 10 mM β-mercaptoethanol, 1 mM EDTA, and 0.1 mM phenylmethanesulfonyl fluoride with 20 units of peptide-N (N-acetylglucosaminyl) asparagine amidase F from *Flavobacterium meningosepticum* (Boehringer Mannheim) (Tarentino, A. L., Gomez, C. M., and Plummer, R. H., Jr., *Biochem.*, 24, 4665–4671 (1985)). For quantitative removal of asparagine-linked oligosaccharides, 10 mg of fetuin was digested with 10 units of enzyme for 48 h at 37° C. Complete release of N-linked sugars was confirmed by change in migration of the protein on SDS gel electrophoresis (Tarentino, A. L., Gomez, C. M., and Plummer, R. H., Jr., *Biochem.*, 24, 4665–4671 (1985)). Following enzyme treatment, protein was precipitated with ethanol and the oligosaccharides released from 500 mg of fetuin were desalted on Sephadex G-25 in 50 mM pyridinium acetate, pH 5, yielding 30 mg of oligosaccharides. The oligosaccharides (13 mg) were fractionated on a 25 ml column of concanavalin A Sepharose. Triantennary oligosaccharides were eluted in the void volume, and the biantennary fraction (0.5 mg) was eluted with 20 mM methyl-α-D-glucoside. The oligosaccharides were desalted by gel filtration and lyophilized. Sialic acid was determined by the periodic acid-resorcinol n assay (Jourdian, G. W., Dean, L. and Roseman, J., *J. Biol. Chem.*, 246, 430–435 (1971)) and carbohydrate compositions was determined by anion exchange chromatography on a Dionex AS-6 column (Hardy, M. R., Townsend, R. R., and Lee, Y. C., *Analyt. Biochem.*, 170, 54–62 (1988)). The triantennary and biantennary fractions contained 3.2 and 1.9 moles of sialic acid per mole oligosaccharide, respectively. Analysis of the sialyloligosaccharides by anion exchange chromatography in 50 mm NaOH with 100 mM sodium acetate on a Dionex AS-6A column confirmed that the biantennary oligosaccharides were quantitatively bound on the con A column and that the biantennary fraction was free of triantennary oligosaccharides. The biantennary fraction eluted as a triplet of peaks on the AS-6A column with similar retention times as authentic biantennary disialyloligosaccharides released from human transferrin and the α-subunit of hCG using peptide-N(N-acetylglucosaminyl) asparagine amidase F (Tarentino, A. L., Gomez, C. M., and Plummer, R. H., Jr., *Biochem.*, 24, 4665–4671 (1985)).

O-linked oligosaccharides from fetuin were released by alkaline borohydride degradation of 20 mg of fetuin pronase-resistant glycopeptides for 16 h at 45° C. in 1M NaBH$_4$, 0.05M NaOH (Edge, A. S. B., and Spiro, R. G., *J. Biol. Chem.*, 262, 16135–16141 (1987)). The reduced sialyloligosaccharides were purified by gel filtration on Biogel P-4 (–400 mesh) eluted with 50 mM pyridinium acetate, pH 5. Hexose and sialic acid were determined using the phenol-sulfuric acid (Dubois, M., Gilles, K. A., Hamilton, J. K., Rebers, P. A. and Smith, F., *Analyt. Chem.*, 28, 350–356 (1956)) and resorcinol (Jourdian, G. W., Dean, L. and Roseman, J., *J. Biol. Chem.*, 246, 430–435 (1971)) assays, respectively.

*M. pneumoniae* adhesion to immobilized glycoproteins.

Glycoproteins dissolved in 0.01M sodium phosphate buffer, pH 7.4, containing 150 mM NaCl, 1 mM CaCl$_2$, and 0.01% NaN$_3$ were adsorbed onto plastic (Falcon 3912 polyvinylchloride 96 well microtiter plates) by incubation for 16 h at 4° C. Immulon 2 Removeawell plates, or Falcon 1007 bacteriological polystyrene were also used in some experiments. The unbound proteins were removed and the wells were filled with tris-BSA and incubated for 30 min at room temperature. The wells were rinsed with RPMI 1640 containing 25 mM HEPES, pH 7.3, and 1% bovine serum albumin (Sigma fatty acid free). *M. pneumoniae* strain M129 labeled with [$^3$H] palmitate (Chandler, D. K. F., Collier, A. M. and Barile, M. F., *Infect. Immun.*, 35, 937–942 (1982)) were dispersed in RPMI-BSA by passing 4 times through a 26 gauge needle and 50 μl of the suspension was applied to the wells. After incubation for 60 min at 37° C., the wells were washed 5 times with saline and the labeled *M. pneumoniae* bound to the proteins were quantified by scintillation counting in Aquasol.

For inhibition studies, sugars in 25 μl of RPMI-BSA were added to wells coated with laminin (10 μg/ml) followed by 25 μl of [$^3$H]-*M. pneumoniae*. Binding was determined to both laminin-coated and uncoated wells in triplicate at each inhibitor concentration and in the absence of inhibitor. In some experiments the adsorbed proteins were pretreated with neuraminidase. After adsorption of the proteins and incubation in tris-BSA, the wells were rinsed 3 times with 50 mM sodium acetate, pH 5.5, containing 150 mM NaCl, 5 mM CaCl$_2$, 1 mg/ml bovine serum albumin, and 1 mM phenylmethanesulfonyl fluoride. The wells were incubated with 0.05 units/ml neuraminidase in the same buffer or with buffer without enzyme overnight at 20° C. The wells were rinsed three times with tris BSA, and *M. pneumoniae* binding was determined as described above.

Binding of monoclonal antibody My-28 (provided by Dr. Curt Civin, Johns Hopkins Oncology Center, Baltimore, Md.) to the immobilized proteins before or after digestion with neuraminidase was determined using a 1:1000 dilution of ascites fluid in tris-BSA. After incubation for 2 h at room temperature, the wells were washed 3 times with tris-BSA. Bound antibody was detected using goat anti-mouse IgM (Kirkegaard and Perry) labeled with $^{125}$I by the Iodogen method (Fraker, P. J. and Speck, J. C., *Biochem. Biophys. Res. Commun.*, 80, 849–857 (1978)).

*M. pneumoniae* adhesion to WiDr cells

Adhesion of labeled *M. pneumoniae* to WiDr cells on glass cover slips was determined as described in the accompanying paper (Krivan, H. C., Olson, L. D., Barile, M. F., Ginsburg, V. and Roberts, D. D.). For inhibition studies, dextran sulfate and 3'-sialyllactose were dissolved in RPMI-BSA and the pH was adjusted to 7.4 with NaOH. The inhibitors were added to wells containing washed cover slips with attached WiDr cells or blank coverslips preincubated in medium or tris-BSA. Labeled *M. pneumoniae* were added immediately and incubated with slow rocking for 60 min at 37°. After washing the coverslips by dipping 6 times in saline, bound *M. pneumoniae* were determined by scintillation counting in Aquasol.

RESULTS

Several glycoproteins including laminin, fetuin, and hCG support dose dependent and saturable adhesion of *M. pneumoniae* when adsorbed on plastic (See FIG. 6). Typically, 20 to 60% of the added *M. pneumoniae* bound to the wells at saturating protein concentrations. Nonspecific binding to uncoated wells was 0.3 to 3% of the total radioactivity applied. As was reported for *M. pneumoniae* attachment to glass substrates (Feldner, J., Bredt. W., and Razin, S., *Infect. Immun.,* 31, 107–113 (1981)) and binding to sulfated glycolipids (Krivan, H. C., Olson, L. D., Barile, M. F., Ginsburg, V. and Roberts, D. D.), binding is energy dependent and no binding was detected in a tris-albumin buffer without glucose. Most proteins, however, are inactive in this assay (FIG. 6 and Table I). The relative activities of several proteins for promoting *M. pneumoniae* adhesion were estimated by comparing the dose response curves and are summarized in Table II.

TABLE II

*M. pneumoniae* binding to glycoproteins adsorbed on plastic

| Protein | Relative binding activity[a] |
|---|---|
| Murine Laminin | 1.5 |
| Bovine Fetuin | 1.0 |
| PNGase F-treated Fetuin | 0.09 |
| hCG | 0.7 |
| hCG α-subunit | 0.8 |
| Human platelet thrombospondin | 0.7 |
| Human type MM glycophorin | 0.06 |
| Human $\alpha_1$-acid glycoprotein | 0.03 |
| Hen Ovomucoid | <0.01 |
| Human Transferrin | <0.01 |
| Human plasma Fibrinogen | <0.01 |
| Human plasma Fibronectin | <0.01 |
| Bovine serum Albumin | <0.01 |

[a]Binding of [$^3$H]-*M. pneumoniae* was determined to polyvinyl chloride microtiter wells coated with 0.006 to 2 μg of the respective proteins. Relative binding activities of the proteins were determined by the amount of protein required to give half maximal binding of labeled *M. pneumoniae* (typically 10–30% of the total added) and are expressed relative to fetuin which was included as a positive control in each experiment and was assigned a value of 1.0. Results are the mean values of 2 or 3 experiments for each protein.

The proteins laminin, fetuin, thrombospondin, hCG, and the α-subunit of hCG have similar activity and promote adhesion to wells coated with less than 10 ng of glycoprotein. Glycophorin and $\alpha_1$-acid glycoprotein are weakly active, whereas the other proteins are essentially inactive, promoting binding of less than 10% of the added *M. pneumoniae* at the highest levels tested (1–5 μg/well).

Immulon 2 microtiter plates and bacteriological polystyrene were also examined as substrates for *M. pneumoniae* adhesion to adsorbed proteins. Although binding varied with the plastic used, the distinction between the active and inactive glycoproteins was consistently observed with all three types of plastic. Thus, the differences in activity are probably not an artifact of selective adsorption of the active glycoproteins.

N-Deglycosylated fetuin was tested in the assay to examine the role of the O-linked sialyloligosaccharides of fetuin in adhesion of *M. pneumoniae* (Table II). The protein promoted adhesion of *M. pneumoniae* at higher concentrations but was approximately 10-fold less active than intact fetuin. The low activity of glycophorin (Table II) also suggests that α2-3-linked sialic acid on O-linked oligosaccharides is not as active as on N-linked oligosaccharides.

Binding to all of the active glycoproteins requires sialic acid, as neuraminidase treatment of the adsorbed proteins (FIG. 7) or pretreatment with neuraminidase in solution before adsorption (results not shown) abolishes all binding activity. Several of the inactive glycoproteins also contain sialic acid but the linkage reported in human transferrin (Spik, G., Bayard, B., Fournet, B., Strecker, G., Bouquelet, S. and Montreuil, J., *FEBS Lett.,* 50, 296–299 (1975)), fibrinogen (Townsend, R. R., Hilliker, E., Li, Y-T., Laine, R. A., Bell, W. R. and Lee, Y. C., *J. Biol. Chem.,* 257, 9704–9710 (1982)), and plasma fibronectin (Takasaki, S., Yamashita, K., Suzuki, K. and Kobata, A., *J. Biochem. Tokyo,* 88, 1587–1594 (1980)) is exclusively α2-6 to galactose. The linkage in hCG (Endo, Y., Yamashita, K., Tachibana, Y., Tojo, S. and Kobata, A., *J. Biochem. Tokyo,* 85, 669–679 (1979)) and a majority of N-linked fetuin oligosaccharides (Nilsson, B., Norden, N. E., and Svensson, S., *J. Biol. Chem.,* 254, 4545–4553 (1979); Takasaki, S. and Kobata, A., *Biochemistry,* 25, 5709–5715 (1986); Townsend, R. R., Hardy, M. R., Wong, T. C. and Lee, Y. C., *Biochemistry,* 25, 5716–5725 (1986)) is α2-3. Thus, in agreement with previous studies of erythrocyte adhesion to surface grown sheet cultures of *M. pneumoniae* (4), binding of the labeled *M. pneumoniae* to immobilized glycoproteins appears to be specific for α2-3-linked sialic acid.

With the exception of hCG, all of the active glycoproteins have extensive heterogeneity in their carbohydrate structures or have only partially characterized structures. hCG contains only mono- and biantennary asparagine-linked oligosaccharides on both subunits (Endo, Y., Yamashita, K., Tachibana, Y., Tojo, S., and Kobata, A., *J. Biochem. Tokyo,* 85, 669–679 (1979); Mizuochi, T. and Kobata, A., *Biochem. Biophys. Res. Commun.,* 97, 772–778 (1980)) and 4 O-linked oligosaccharides on the β-subunit (Kessler, M. J., Mise, T., Ghai, R. D., and Bahl, O. P., *J. Biol. Chem.,* 254, 7909–7914 (1979)). Since the α-subunit of hCG binds *M. pneumoniae* as well as the intact protein (Table I and FIG. 7), the O-linked carbohydrates on the β-subunit are not required for binding. Thus, a biantennary asparagine linked carbohydrate with α2-3-linked sialic acid is sufficient for binding of *M. pneumoniae.*

EXAMPLE 3

In generally the same manner as described above various bacteria were tested for their ability to bind to GalNAcβ1-4Gal sequences found in fucosylasialo-GM1, asialo-GM1 and asialo-GM2. The results are shown in the following table.

| Microorganism | Binding* |
|---|---|
| *Streptococcus pneumoniae* 33400 | + |
| *Streptococcus pneumoniae* 6303 | + |
| *Streptococcus pneumoniae* 27336 | + |
| *Staphylococcus aureus* 12600 | + |
| *Staphylococcus aureus* 8095 | + |
| *Haemophilus influenzae* 33391 | + |
| *Haemophilus influenzae* 9795 | + |
| *Haemophilus parainfluenzae* 33392 | + |
| *Klebsiella pneumoniae* 27736 | + |
| *Pseudomonas aeruginosa* CT3 | + |
| *Pseudomonas aeruginosa* CT4 | + |
| *Pseudomonas aeruginosa* CT5 | + |
| *Pseudomonas aeruginosa* 17648 | + |
| *Pseudomonas aeruginosa* 19142 | + |
| *Pseudomonas aeruginosa* 33347 | + |
| *Pseudomonas aeruginosa* 21472 | + |
| *Pseudomonas cepacia* 25416 | + |
| *Pseudomonas cepacia* ML1 | + |
| *Pseudomonas cepacia* 13945 | + |
| *Pseudomonas maltophilia* 13637 | + |

| Microorganism | Binding* |
|---|---|
| *Escherichia coli* VJ1 | + |
| *Escherichia coli* 6883 | + |
| *Mycoplasma pneumoniae* M129 | − |
| *Streptococcus pyogenes* 12344 | − |
| *Salmonella milwaukee* U4 4407-50 | − |
| *Salmonella enteritidis* 13076 | − |
| *Escherichia coli* K1 | − |
| *Escherichia coli* K99 1472 (B44) | − |

*Bacteria were tested for binding to glycosphingolipids by the bacterial overlay assay. Plus (+) indicates binding and minus (−) indicates no binding to at least 2 μg of glycosphingolipid containing the GalNAcβ1–4Gal sequence.

EXAMPLE 4

Figure 10:
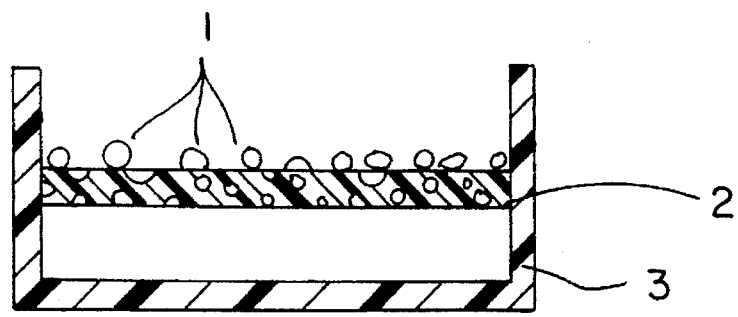
FIG. 10 is a cross-sectional view of a preferred device for practicing the invention.
Figure 6:
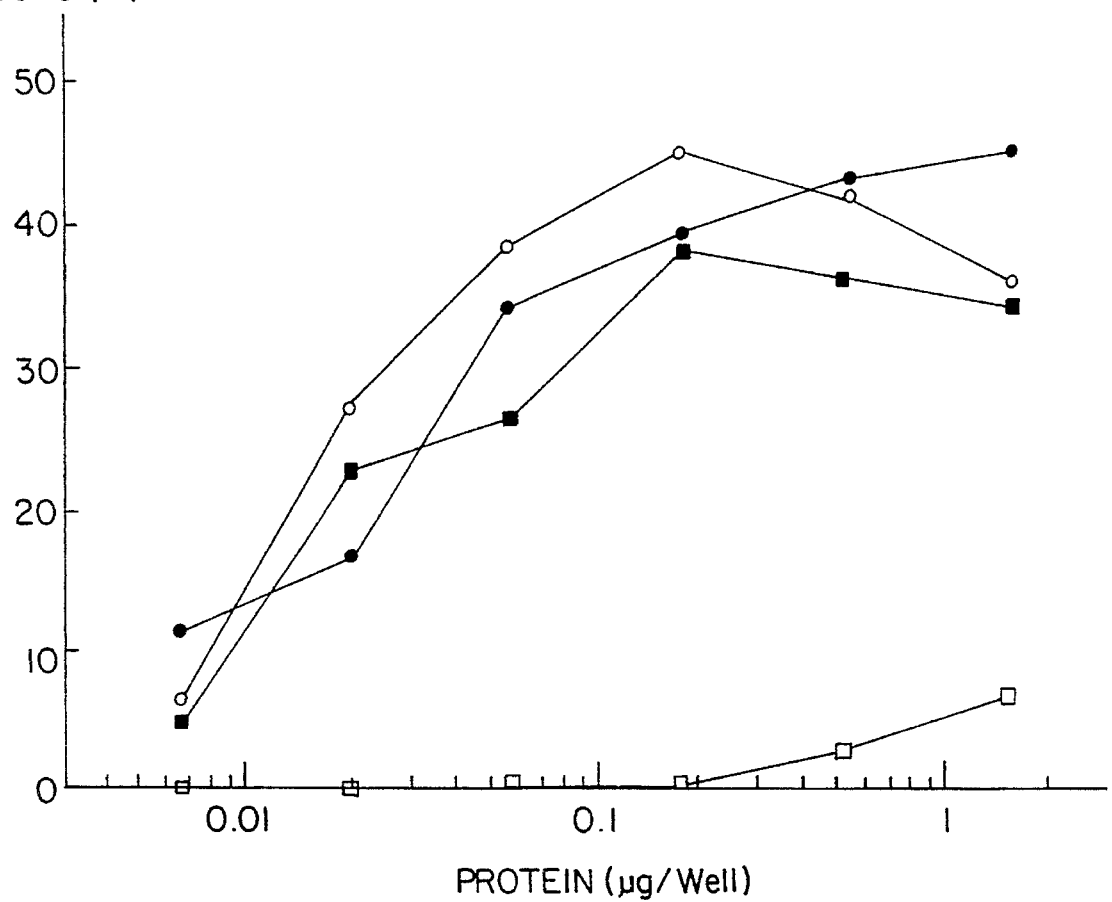
FIG. 6. *M. pneumoniae* binding to immobilized glycoproteins. [$^3$H]-labeled *M. pneumoniae*, 630,000 cpm/5×10$^5$ CCU, were incubated for 60 min at 37° C. in microtiter wells coated in duplicate with laminin (solid circle), fetuin (open circle), hCG (solid square), or transferrin (open square) at the indicated concentrations. After washing to remove the unbound organisms the bound *M. pneumoniae* were determined by scintillation counting. Binding to uncoated wells was 3% of the applied radioactivity.
Figure 7:
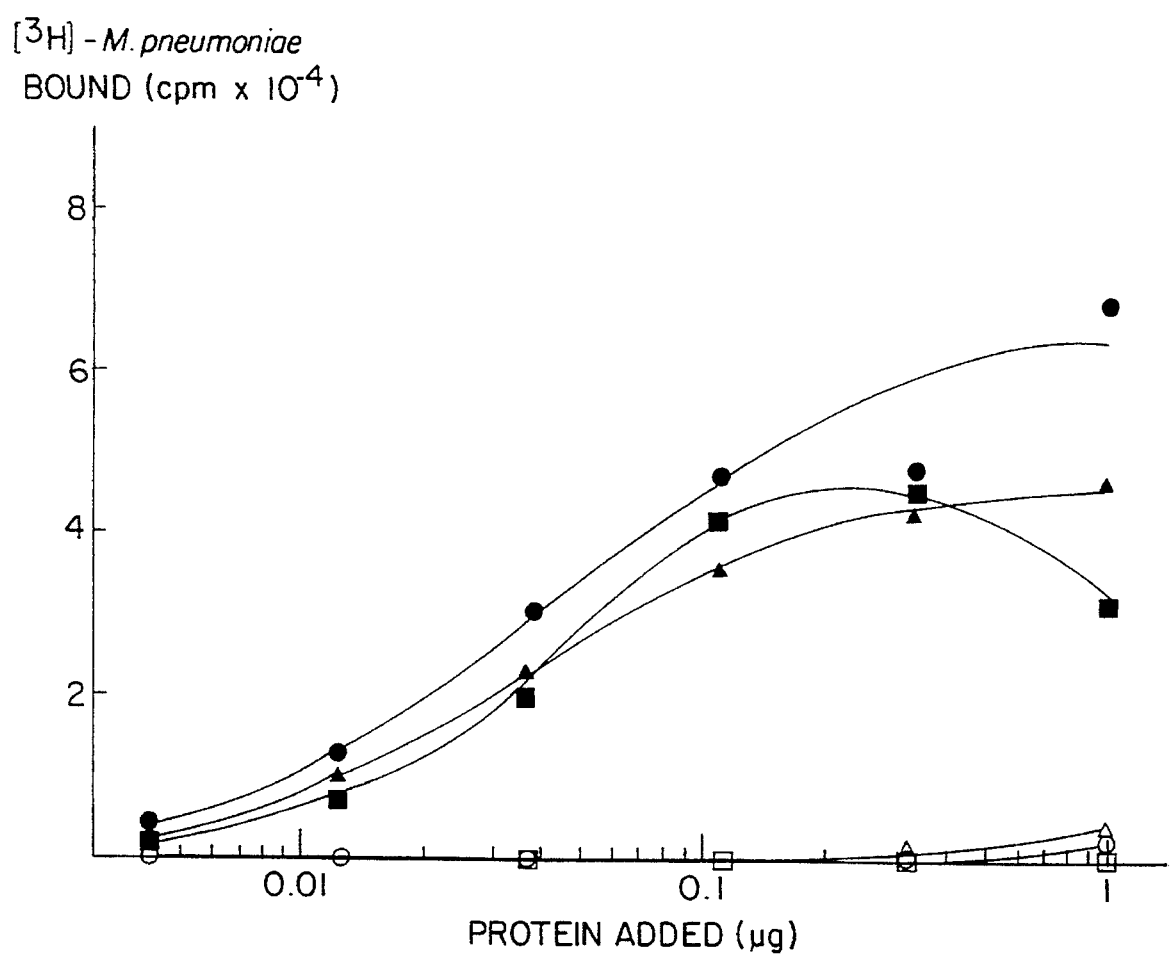
FIG. 7. Effect of neuraminidase treatment on *M. pneumoniae* binding to immobilized glycoproteins. Microtiter wells were coated with fetuin (circles), hCG (squares), or α-subunit of hCG (triangles) and treated for 16 h with 0.05 U/ml neuraminidase (open symbols) in sodium acetate buffer pH 5.5 or buffer alone (closed symbols). [$^3$H]-labeled *M. pneumoniae* binding was determined as described in Materials and Methods.
Figure 8:
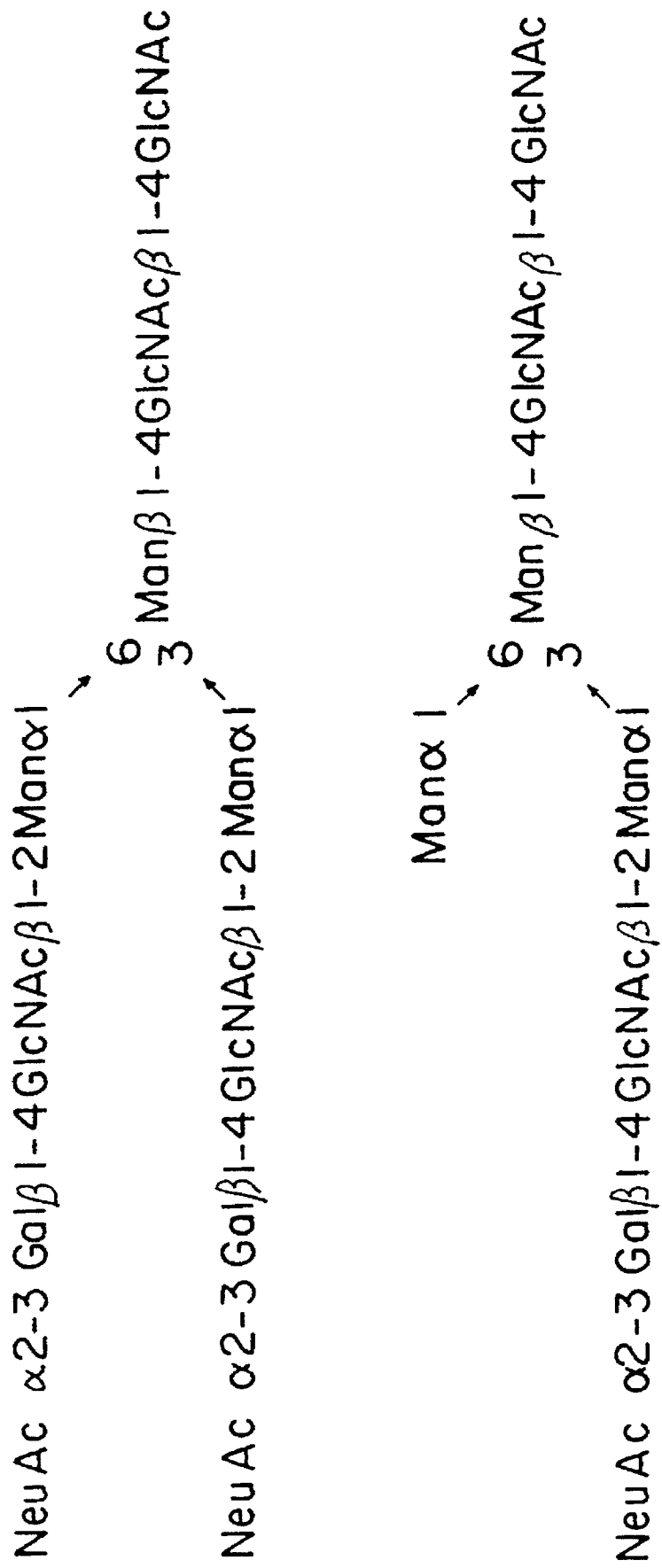
FIG. 8. Structures of sialylated oligosaccharides on the α subunit of human chorionic gonadotropin (23) proposed to mediate *M. pneumoniae* adhesion. The biantennary oligosaccharide is the minimal structure required for binding based on the present results. It is not known whether the monoantennary oligosaccharide can bind *M. pneumoniae* with high affinity.
Figure 9:
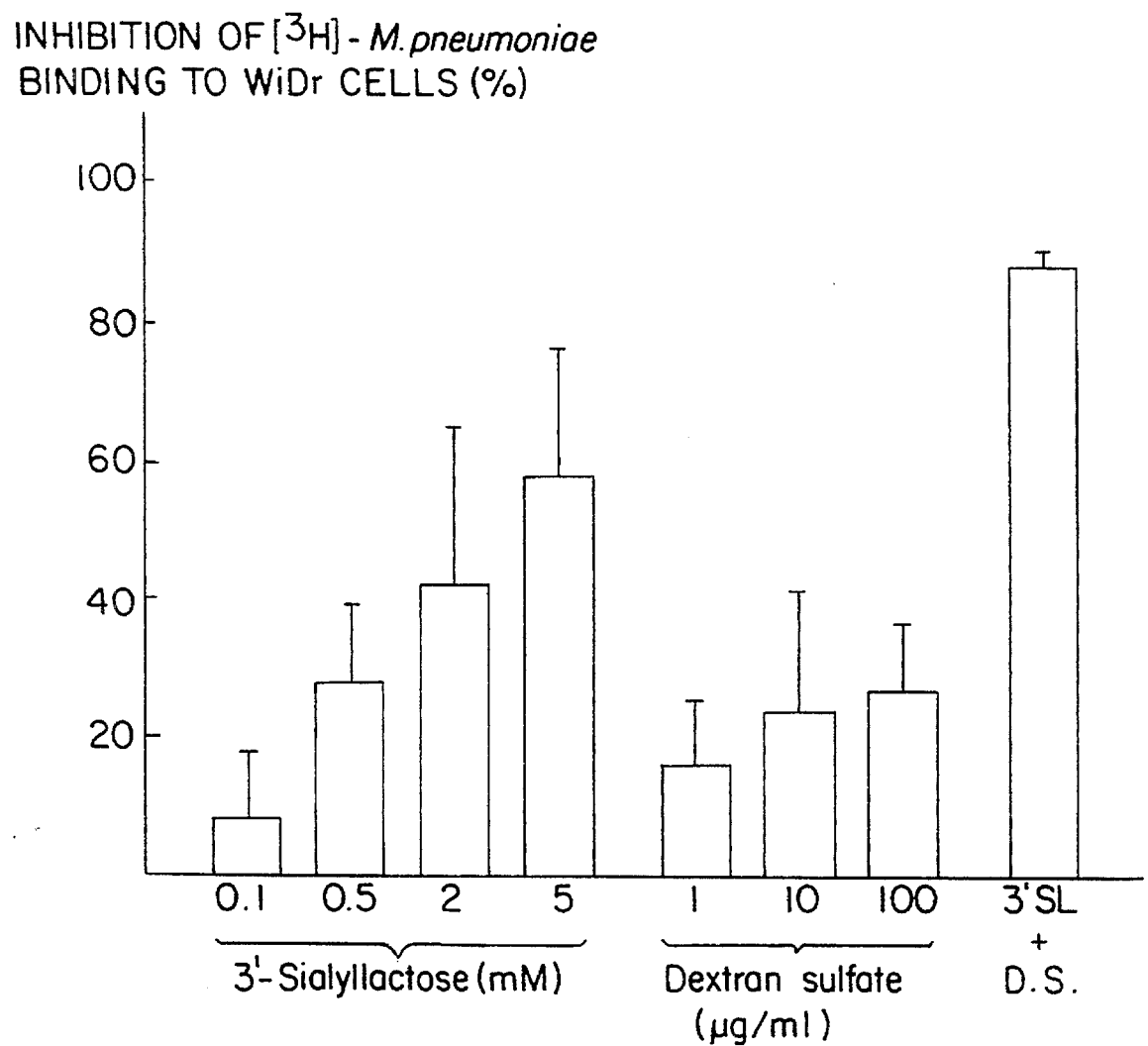
FIG. 9. Inhibition of *M. pneumoniae* adhesion to the human adenocarcinoma WiDr cell line. Adhesion of [$^3$H]-*M. pneumoniae* to WiDr cells growing on 13 mm glass cover slips was determined as described in Materials and Methods. Inhibition by dextran sulfate or 3'-sialyllactose at the indicated concentrations or by a combination of 100 μg/ml dextran sulfate and 5 mM 3'-sialyllactose (3'S L+D.S.) was calculated relative to control binding determined in RPMI/BSA without inhibitors. Results are presented as percent inhibition (mean ±S.D. n=4 with n=8 for determination of control binding without inhibitors).

The following predictive Example constitutes a preferred manner for carrying out the present invention as shown in FIG. 10. Latex particles 1 coated with carbohydrate receptors which bind to *E. coli* (prepared by the method described by de Man et al, *J. Clin. Micb.*, 25, 401–406 (1987), the entire contents of which are hereby incorporated by reference) are immobilized on a porous membrane 2 which is supported in a container 3. The particles are present in an amount sufficient to bind *E. coli* which may contact the particles but not in an amount so great as to "clog" the membrane or destroy its porosity. A liquid sample suspected of containing *E. coli* is poured onto the top of the membrane and passes across said latex particles and through said porous membrane whereby *E. coli*, if present, will adsorb to the carbohydrate receptors on the latex particles. A solution containing a labelled antibody against *E. coli* (e.g., an antibody conjugated to an enzyme) is then passed across said latex particles and through said membrane. A wash solution is then passed across said latex particles and through said membrane to wash any unbound labelled antibody off the membrane. If the label is an enzyme, a substrate for said enzyme is then contacted with said membrane. If the enzyme conjugated antibody is bound in said membrane to the latex particles, the enzyme substrate will turn color thereby indicating the presence of the microorganisms. If the label is a fluorescent or radioactive material, another suitable test is employed to detect the presence of the labelled antibody.

In order to treat a patient infected with *Mycoplasma hominus* or *Mycoplasma pneumoniae,* a compound of the present invention is combined with a pharmaceutically acceptable carrier and administered to a patient in an amount sufficient to bind the pathogen and remove it from the system of the patient. These amounts, which are readily determined by those skilled in the art, can range from approximately 0.1 gram to about 5 grams per patient per day until there is evidence of successful treatment of the infection.

Compositions within the scope of the invention include compositions wherein the active ingredient is contained in an effective amount to achieve its intended purpose. Determination of the effective amount is, of course, within the skill in the art.

In addition to the active Mycoplasma binding compound, the pharmaceutical compositions according to the present invention may contain suitable pharmaceutically acceptable carriers comprising excipients and auxiliaries which facilitate processing of the active ingredients into preparations which can be used pharmaceutically to treat infection with the *Mycoplasma* pathogens.

Preferably, the preparations, particularly those which can be administered orally and which can be used for the preferred type of administration, such as tablets, dragees, capsules, and preparations which can be administered rectally, such as suppositories, as well as suitable solutions for administration orally or by injection, contain from about 0.1 to about 99 percent, and preferably from about 25–85 percent, of active ingredient, together with the excipient.

The pharmaceutical preparations of the present invention are manufactured in a manner which is itself known, such as by means of conventional mixing, granulating, dragee-making, dissolving or lyophilizing. The pharmaceutical preparations for oral use can be obtained by combining the active ingredients with solid excipients and processing the compounds, after adding suitable auxiliaries, if desired or necessary, to obtain tablets or dragee cores.

Suitable excipients include filler such as sugars, for example, lactose, sucrose, mannitol, or sorbitol, cellulose preparations and/or calcium phosphates, such as iricalcium phosphate or calcium hydrogen phosphate, as well as binders such as starch paste using starches such as maize starch, wheat starch, rice starch, potato starch, gelatin, gum tragacanth, methyl cellulose, hydroxypropylcellulose, sodium carboxymethylcellulose, and/or polyvinylpyrrolidone. If desired, disintegrating agents may be added, such as the above-mentioned starches and carboxymethyl starch, crosslinked polyvinyl pyrrolidone, agar, alginic acid or a salt thereof, such as sodium alginate. Auxiliaries are, above, all, flow-regulating agents and lubricants, such as silica, talc, stearic acid or salts thereof, and/or polyethylene glycol. Dragee cores are provided with suitable coatings which, of desired, are resistant to gastric juices. For this purpose, concentrated sugar solutions may be used, which may optionally contain gum arabic, talc, polyvinyl pyrrolidone, polyethylene glycol and/or titanium dioxide, lacquer solutions, and suitable organic solvents or solvent mixtures. In order to produce coatings resistant to gastric juices, solutions of suitable cellulose preparations such as acetyl-cellulose phthalate or hydroxy-propylmethylcellulose phthalate are used. Dyestuffs or pigments may be added to the tablets or dragee coatings, for example, for identification or in order to characterize different combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition, stabilizers may be added.

Possible pharmaceutical preparations which can be used rectally include, for example, suppositories, which consist of a combination of the active compounds in a suppository base. Suitable suppository bases are, for example natural or synthetic triglycerides, paraffin, hydrocarbons, polyethylene glycols or higher alkanols. In addition, it is also possible to use gelatin rectal capsules which consists of a combination of the active compounds with a base. Possible base materials include, for example, liquid triglycerides, polyethylene glycols, or paraffin hydrocarbons.

Suitable formulations for parenteral administration and irrigation of diseased tissues include aqueous solutions of the active ingredients in water-soluble form. In addition, suspensions of the active ingredients as appropriate oily injection suspensions may be administered. Suitable lipophilic solvents or vehicles include fatty oils, such as sesame oil, or synthetic fatty acid esters, such as ethyl oleate or triglycerides. Aqueous injection suspensions may contain substances which increase the viscosity of the suspension, such as sodium carboxy-methyl cellulose, sorbitol, and/or dextran. Optionally, the suspension contains stabilizers.

Compositions prepared according to the present invention are used to treat patients infected with one of the *Mycoplasma* pathogens, such as *M. pneumoniae* or *M. hominus*. A composition according to the present invention is administered to the patient for the duration of appearance of symptoms of infection. This time period is determined without undue experimentation by one skilled in the art. Determination of infection can be accomplished by detecting the pathogens in sample of bodily fluid from the patient or from examining the clinical symptoms of infection, such as fever, shivering, etc.

Diseased tissue can be irrigated with a liquid composition containing the compounds of the present invention to remove any Mycoplasma pathogens from the tissue. Preferably, a dilute solution containing approximately 0.1 to 5 grams per liter of the active ingredient is contained in a pharmaceutically acceptable carrier, such as saline solution. Irrigation of the tissue is continued until there appear to be no further pathogens present in the tissue.

What is claimed is:

1. A composition for binding mycoplasmas comprising a carbohydrate receptor or human platelet thrombospondin bound to an insoluble support, wherein said carbohydrate receptor is selected from the group consisting of Gal(SO$_4$)β1-1Cer, Gal(6SO$_4$)β1-1Cer and Gal(3SO$_4$)β1-4Glcβ1-1Cer.

2. The composition of claim 1, wherein said insoluble support comprises a latex particle.

3. A diagnostic kit for detecting a mycoplasma comprising:

a carbohydrate receptor or glycoprotein bound to an insoluble support, wherein said carbohydrate receptor is selected from the group consisting of Gal(SO$_4$)β1-1Cer, Gal(3SO$_4$)β1-1Cer, Gal(6SO$_4$)β1-1Cer, Gal(3SO$_4$)β1-4Glcβ1-1Cer, and Gal(3SO$_4$)β1- 3alkylacylglycerol and wherein said glycoprotein is a glycoprotein containing a biantennary oligosaccharide wherein both branches of said oligosaccharide terminate with α2-3-linked sialic acid; and a labeled reagent for detecting a mycoplasma bound to said carbohydrate receptor or said glycoprotein.

4. The diagnostic kit of claim 3, wherein said labeled reagent is a labeled antibody that binds to said mycoplasma.

5. The diagnostic kit of claim 3, wherein said labeled reagent is a labeled carbohydrate receptor that binds to said mycoplasma.

6. The diagnostic kit of claim 5, wherein said labeled carbohydrate receptor is labeled with an enzyme, a radioactive material, or a fluorescent material.

7. The diagnostic kit of claim 3, wherein said labeled reagent is a labeled glycoprotein receptor that binds to said mycoplasma.

8. The diagnostic kit of claim 3, wherein said labeled reagent comprises a first antibody that binds to said mycoplasma and a second labeled antibody that binds to said first antibody.

9. A pharmaceutical composition comprising a carbohydrate receptor or human platelet thrombospondin in a pharmaceutically acceptable carrier, wherein said carbohydrate receptor is selected from the group consisting of Gal(SO$_4$)β1-1Cer, Gal(6SO$_4$)β1-1Cer and Gal(3SO$_4$)β1-4Glcβ1-1Cer.

10. The pharmaceutical composition of claim 9, wherein said pharmaceutically acceptable carrier is soluble in water.

11. The pharmaceutical composition of claim 9, wherein said pharmaceutically acceptable carrier is insoluble in water.

12. A method for removing a mycoplasma from a sample comprising the steps of:

contacting said sample with a compound selected from the group consisting of dextran sulfate, Gal(SO$_4$)β1-1Cer, Gal(3SO$_4$)β1-1Cer, Gal(6SO$_4$)β1-1Cer, Gal(3SO$_4$)β1-4Glcβ1-1Cer, and Gal(3SO$_4$)β1- 3alkylacylglycerol wherein said compound is bound to an insoluble support;

incubating said sample with said compound for a period of time and under conditions sufficient to bind said mycoplasma to said compound; and removing said insoluble support, having said mycoplasma bound thereto, from said sample.

13. The method of claim 12, wherein said insoluble support is a chromatography column.

14. A method for detecting a mycoplasma in a sample comprising the steps of:

contacting said sample with a carbohydrate receptor or a glycoprotein effective for specifically binding a mycoplasma, bound to an insoluble support, wherein said carbohydrate receptor is selected from the group consisting of dextran sulfate, Gal(SO$_4$)β1-1Cer, Gal(3SO$_4$)β1-1Cer, Gal(6SO$_4$)β1- 1Cer, Gal(3SO$_4$)β1-4Glcβ1-1Cer, and Gal(3SO$_4$)β1-alkylacylglycerol and wherein said glycoprotein is a glycoprotein containing a biantennary oligosaccharide wherein both branches of said oligosaccharide terminate in α2-3-linked sialic acid, for a time and under conditions sufficient for said mycoplasma in said sample to bind to said carbohydrate or glycoprotein receptor, thereby forming a complex on said support;

contacting said complex with a labeled reagent that binds to said mycoplasma for a period of time and under conditions sufficient for said labeled reagent to bind to said mycoplasma in said complex; and detecting the presence of said labeled reagent bound to said mycoplasma in said complex, thereby detecting the presence of said mycoplasma in said sample.

15. A method for detecting a mycoplasma in a sample comprising the steps of:

contacting said sample with a glycoprotein bound to an insoluble support for a time and under conditions sufficient for said mycoplasma in said sample to bind to said glycoprotein, thereby forming a complex on said support, wherein said glycoprotein is selected from the group consisting of laminin, fetuin, human chorionic gonadotropin, the alpha subunit of human chorionic gonadotrophin, and human platelet thrombospondin, contacting said complex with labeled dextran sulfate for a period of time and under conditions sufficient for said dextran sulfate to bind to said mycoplasma in said complex; and detecting the presence of said labeled dextran sulfate bound to said mycoplasma in said complex, thereby detecting the presence of said mycoplasma in said sample.

16. The method of claim 15, wherein said glycoprotein is fetuin.

17. The method of claim 16, wherein said labeled dextran sulfate is an enzyme-dextran sulfate conjugate.

18. A method for inhibiting the binding of mycoplasmas to cells comprising contacting said cells or said mycoplasmas with an effective amount of a compound selected from the group consisting of dextran sulfate, Gal(SO$_4$)β1-1Cer, Gal(3SO$_4$)β1-1Cer, Gal(6SO$_4$)β1- 1Cer, Gal(3So$_4$)β1-4Glcβ1-1Cer, Gal(3SO$_4$)β1 -3alkylacylglycerol, and a glycoprotein containing an α2-3-linked sialyloligosaccharide.

19. A composition for binding mycoplasmas comprising a carbohydrate receptor bound to an insoluble support, wherein said carbohydrate receptor is selected from the group consisting of Gal(SO$_4$)β1-1Cer, Gal(6SO$_4$)β1-1Cer, Gal(3SO$_4$)β1-4Glcβ1 -1Cer and a biantennary oligosaccharide wherein both branches of said oligosaccharide terminate with α2-3-linked sialic acid.

* * * * *